(12) United States Patent
Kirk et al.

(10) Patent No.: US 8,178,860 B2
(45) Date of Patent: May 15, 2012

(54) IMAGE COLLECTION

(75) Inventors: Gregory L. Kirk, Pleasanton, CA (US); Matthew W. Derstine, Los Gatos, CA (US); Shiow-Hwei Hwang, San Ramon, CA (US); Isabella T. Lewis, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 530 days.

(21) Appl. No.: 12/545,042

(22) Filed: Aug. 20, 2009

(65) Prior Publication Data

US 2011/0043797 A1   Feb. 24, 2011

(51) Int. Cl.
*G01N 21/88* (2006.01)
(52) U.S. Cl. .......... 250/559.45; 356/237.5; 382/145
(58) Field of Classification Search ............ 250/559.42, 250/559.48, 559.45; 356/237.1–237.6, 367–369, 356/625–629; 359/388, 385, 368; 382/141, 382/145, 149, 245, 266
See application file for complete search history.

(56) References Cited

U.S. PATENT DOCUMENTS

| | | | |
|---|---|---|---|
| 6,700,658 B2 * | 3/2004 | Leonard | 356/237.1 |
| 6,900,888 B2 * | 5/2005 | Yoshida et al. | 356/237.4 |
| 6,909,501 B2 | 6/2005 | Ogawa et al. | |
| 7,463,350 B2 | 12/2008 | Nishiyama et al. | |
| 2007/0070337 A1 | 3/2007 | Ohshina et al. | |
| 2007/0215575 A1 | 9/2007 | Gu et al. | |

FOREIGN PATENT DOCUMENTS

JP   59-208408 A   11/1984

* cited by examiner

*Primary Examiner* — Tony Ko
(74) *Attorney, Agent, or Firm* — Luedeka Neely Group, P.C.

(57) ABSTRACT

An inspection system for creating images of a substrate. A light source directs an incident light onto the substrate, and a light source timing control controls a pulse timing of the incident light. A stage holds the substrate and moves the substrate under the incident light, so that the substrate reflects the incident light as a reflected light. A stage position sensor reports a position of the stage, and a stage position control controls the position of the stage. A time domain integration sensor receives the reflected light, and a time domain integration sensor timing control controls a line shift of the time domain integration sensor. A control system is in communication with the light source timing control, the stage position control, and the time delay integration sensor timing control, and sets the pulse timing of the incident light, the position of the stage, and the line shift of the time delay integration sensor, such that a single line of the time domain integration sensor integrates reflected light from more than one pulse of the incident light from the light source.

18 Claims, 1 Drawing Sheet

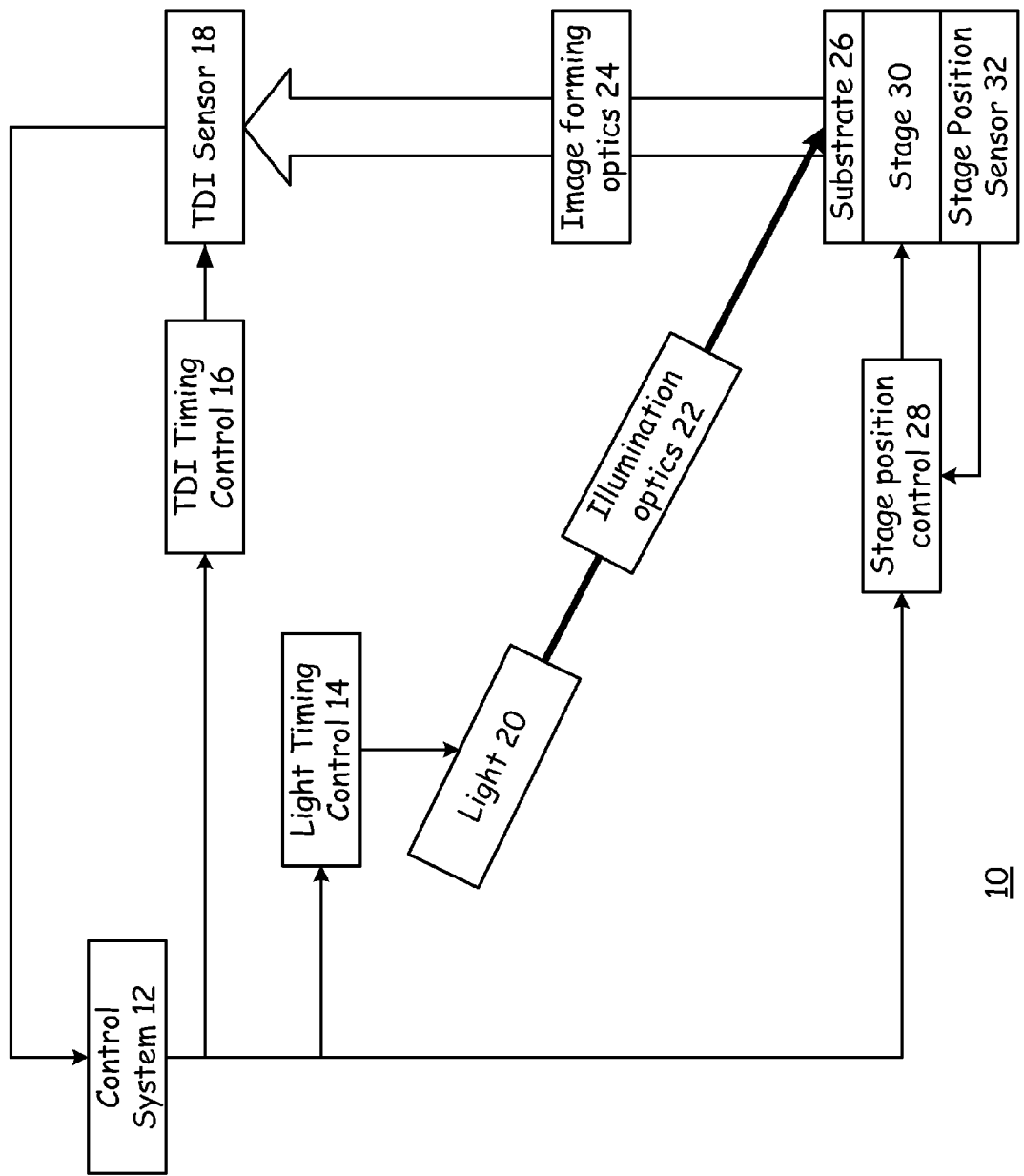

IMAGE COLLECTION

FIELD

This invention relates to the field of integrated circuit fabrication. More particularly, this invention relates to substrate inspection systems.

BACKGROUND

Substrate inspection systems are extensively employed in the integrated circuit fabrication industry to detect defects in substrates. These systems operate by directing a light, such as a laser light, onto the substrate, sensing properties of the reflected or scattered light, converting the sensed properties into electrical signals, converting those signals to information in a memory, and then comparing the gathered information to some kind of reference information, be it historical or otherwise, to determine various properties of the measured substrate. The reference information can come from other measurements of the substrate or from some other source of information.

As the term is used herein, "substrate" includes reticles and masks that are used to pattern integrated circuits, and the wafers—either semiconducting or insulating—upon which the integrated circuits are fabricated. "Integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

To detect the relatively small defects that are found in the commensurately small geometries of modern integrated circuits, the resolution of the inspection system needs to be commensurately high. This is typically accomplished by providing a light having a wavelength that is small enough to observe these small defects. Q-switched or excimer lasers are available at wavelengths such as 213 nanometers, 193 nanometers, and 157 nanometers, which are sufficiently small as to be able to detect the small defects within a modern integrated circuit. However, currently inspection system architectures that employ low repletion rate optical sources require high optical powers in a single pulse. For a high throughput inspection system with a high sensitivity, the required power level from a q-switched or excimer laser can be high enough to damage the substrate that is being inspected. Further, these high peak powers can be sufficient to damage the optics used to illuminate the substrate and collect the reflected and scattered light.

In addition, q-switched and excimer lasers, flashlamps, and pulsed plasma extreme ultraviolet light sources tend to exhibit large pulse-to-pulse variations in power. This variation can be difficult to compensate for in the comparison process, and tends to reduce the sensitivity of the detection process. Such lasers also tend to exhibit speckle in the illumination, and this variation of in the illumination across the surface of the substrate also reduces the detection sensitivity.

What is needed, therefore, is a system that overcomes problems such as those described above, at least in part.

SUMMARY

The above and other needs are met by an inspection system for creating images of a substrate. A light source directs an incident light onto the substrate, and a light source timing control controls a pulse timing of the incident light. A stage holds the substrate and moves the substrate under the incident light, so that the substrate reflects the incident light as a reflected light. A stage position sensor reports a position of the stage, and a stage position control controls the position of the stage. A time domain integration sensor receives the reflected light, and a time domain integration sensor timing control controls a line shift of the time domain integration sensor. A control system is in communication with the light source timing control, the stage position control, and the time delay integration sensor timing control, and sets the pulse timing of the incident light, the position of the stage, and the line shift of the time delay integration sensor, such that a single line of the time domain integration sensor integrates within a single line shift reflected light from more than one pulse of the incident light from the light source.

In this manner, the light source can be operated at a power that is low enough so as to be better controlled and to not damage either optics of the system or the substrate, but where more than one pulse of the light source is integrated by the time domain integration sensor, and a good image of the substrate is produced. In some embodiments the light source is at least one of an excimer laser, a q-switched laser, and a flash lamp. In some embodiments the pulse timing of the light source is an integer multiple of the line shift of the time domain integration sensor. In some embodiments the light source pulse rate is sufficiently accurate that only the stage and the time domain integration sensor are synchronized.

BRIEF DESCRIPTION OF THE DRAWINGS

Further advantages of the invention are apparent by reference to the detailed description when considered in conjunction with the figure, which is not to scale so as to more clearly show the details, wherein like reference numbers indicate like elements, and which depicts a functional block diagram of an inspection system according to an embodiment of the present invention.

DETAILED DESCRIPTION

One aspect of the various embodiments of the present invention is the proper synchronization of the various subsystems in a substrate inspection system, which enable the use of q-switched and excimer lasers, despite their previous limitations as applied to prior art systems. With reference now to the figure, there is depicted a functional block diagram of an inspection system 10 according to an embodiment of the present invention. The inspection system 10 includes a light source 20, such as a q-switched or excimer laser or a flash lamp, that is directed through illumination optics 22 toward a substrate 26. Scattered light from the substrate 26 is collected by image forming optics 24, which focus an image of the substrate 26 onto a time domain integration sensor 18, which sends the image information to a control system 12 for processing and analysis.

The timing of the pulses from the light 20 and the timing of the row shift of the time domain integration sensor 18 are under the direction of the control system 12. The control system 12 is in communication with a light timing control module 14, by which the timing of the light 20 is controlled. The control system 12 sends commands to a stage position control 28, which controls the position of a movable stage 30, upon which the substrate 26 is disposed. The stage position control 28 receives information about the stage 30 position from a sensor 32, and can report the position information back to the control system 12. The control system 12 in some embodiments also receives programmable instructions from an operator, such as through a keyboard or touch screen input, or remotely such as through a network interface.

In the inspection system 10, the light 20 is pulsed (not operated in a continuous wave mode) at a relatively low frequency, such as from about 100 hertz to about 300 kilohertz, such that each line frame that is sent from the time domain integration sensor 18 to the control system 12 includes light received from more than one pulse of the light 20. In prior art systems, a single light pulse was captured by a single scan frame of a light sensor, which created problems, such as those described in the background section.

However, one of the aspects of the embodiments of the present invention is that more than one light pulse is captured in a single scan frame line of the time domain integration sensor 18, and thus the intensity of each pulse can be lower, such that the substrate 26 and the optics 22 and 24 (or other portions of the system 10) are not damaged. The lower pulse intensity also provides for added control over the intensity of the light pulses. However, by capturing more than one light pulse with a single scan frame of the sensor 18, a sufficient amount of light is captured to make a good image of the substrate 26. Further, by digitizing the information from several light pulses in a single scan frame of the sensor 18, there is also realized a general reduction in the inherent background noise.

In other words, embodiments of the present invention use a time domain integration sensor 18 with a line rate that is less than the pulse repetition rate of the light 20, to collect light from multiple light pulses. This keeps the peak power low on the substrate 26 and allows for averaging of the images to correct for variations in the illumination power. One advantage of this method is that the averaging is done directly with the analog charges. Thus, the noise that is added by the analog to digital conversion is only done once for multiple light pulses.

To further explain, embodiments according to the present invention allow charges to accumulate within a time domain integration sensor for multiple bursts of light, then digitize the sensor levels and read into memory the resultant digitized sensor levels. Thus, the accumulation or averaging is accomplished in the analog sensor itself. This is distinguished from a process where a sensor is exposed to a single burst of light, then the sensor level is digitized and read into memory, the sensors are then nominalized and the exposure and storage process is repeated some number of times, and then the digitized values in the memory are summed or averaged. That process of accumulation or averaging is memory-based, while the embodiments of the present invention for accumulation or averaging are sensor-based.

The embodiments of the present invention enable a pulsed light 20 of the type described above to be used with an inspection system 10 having a time delay integration sensor 18. This has not formerly been possible because of the high variability in the signal level, which is a result of the unpredictability of the amount of light that is collected by the time delay integration sensor 18. The embodiments of the present invention resolve that unpredictability.

As the stage 30 moves and a feature on the substrate 26 moves across the field of view of the time domain integration sensor 18, the light pulses illuminate the feature and the light is integrated as the charge moves across the time domain integration sensor 18. In some embodiments the stage 30 moves at a constant speed, the light 20 is pulsed at a fixed rate, and the time domain integration sensor 18 line rate is constant, so that the constant intervals of the light 20 pulses cause the light to integrate within the correct pixel of the time domain integration sensor 18. In some embodiments, the inspection system 10 has a clocking mechanism for the time domain integration sensor 18, which clocking mechanism is synchronized to the motion of the stage 30 (using pulses generated from the stage position sensor 32) so that the time domain integration sensor 18 clocks the pixels as the stage 30 moves through the appropriate distance, even if the speed varies, in order to preserve image quality.

In some embodiments the pulsed light 20 is locked to the motion of the stage 30 so that it pulses at intervals determined by the motion of the stage 30. This assures that the number of light pulses remains an integer and the amount of light on all pixels of the time domain integration sensor 18 remains the same.

A further refinement stabilizes the amount of light in a given image by tracking the variations in pulse energy of the light 20. For one pulse or n pulses, the energy per pulse is monitored and the image data is scaled to compensate for relative variations. These variations can be tracked, for example, with a separate detector or an image mean value calculation that is synchronized with the line groupings of the discreet pulse intervals. Compensation of the varying light energy can be accomplished by direct scaling of the signal levels in the sensor 18, in an interface board, or in the image processor in the control system 12, or by histogram remapping in algorithms for comparison.

Stage Output Information

The motion of the stage 30 is monitored with the stage position sensor 32, which in various embodiments includes devices such as optical scales and interferometers. Both of these methods provide a pulsed output as the stage 30 moves. The stage position control system 28 can also translate the raw information from the interferometer (for example) to a higher or lower frequency pulse frequency. This rate could be some multiple of the clock rate used by the time domain integration sensor 18.

Locking Stage Position & Laser Pulses to Time Domain Integration Sensor

Both excimer lasers and q-switched lasers typically operate by using an external clock to initiate the large currents that are needed to drive the electrical discharge for the excimer lasers or to drive the optical switch that is used to initiate the lasing in a q-switched laser. Because these clocks are not locked to any internal optical processes, these pulses can vary slightly in time. In some embodiments, the precise time of the laser pulses is adjusted to track the speed of the stage 30.

The light 20 can produce a number of pulses between each line rate of the time domain integration sensor 18. By locking the laser pulse rate to the line rate and phase, the number of pulses per pixel remains constant. Thus, systematic variations from different illumination levels can be minimized while still enabling averaging of a number of pulses.

The simplicity of q-switching and excimer laser processes means that more laser wavelengths can be used for inspection. For example, extreme ultra violet (13.5 nanometer) pulsed-plasma sources can be used to expose substrates, and new inspection systems can be developed to find defects on substrates using similar pulsed plasma sources. The concepts described in this application apply equally to pulsed extreme ultraviolet light sources.

Several alternatives are available for the light 20, including diode pumped crystal q-switched lasers with frequency multiplication, diode pumped q-switched fiber lasers with frequency multiplication, flash lamp pumped crystal q-switched with frequency multiplication, direct flash lamp illumination, pulsed light emitting diodes, and extreme ultraviolet pulsed plasma sources, including laser produced plasma and discharge produced plasma.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An inspection system for creating images of a substrate, the inspection system comprising:
   a light source for directing an incident light onto the substrate,
   a light source timing control for controlling a pulse timing of the incident light,
   a stage for holding the substrate and moving the substrate under the incident light, the substrate thereby reflecting the incident light as a reflected light,
   a stage position sensor for reporting a position of the stage,
   a stage position control for controlling the position of the stage,
   a time domain integration sensor for receiving the reflected light,
   a time domain integration sensor timing control for controlling a line shift of the time domain integration sensor, and
   a control system in communication with the stage position control and the time delay integration sensor timing control, for setting the position of the stage and the line shift of the time delay integration sensor, such that the stage and the time delay integration sensor integrates within a single line shift reflected light from more than one pulse of the incident light from the light source to form an image.

2. The inspection system of claim 1, wherein the light source is at least one of an excimer laser, a q-switched laser, extreme ultraviolet pulsed plasma, and a flash lamp.

3. The inspection system of claim 1, wherein the pulse timing of the light source is an integer multiple of the line shift of the time domain integration sensor.

4. The inspection system of claim 1, wherein the control system is in communication with the light source timing control.

5. The inspection system of claim 1, wherein:
   the light source is at least one of an excimer laser, a q-switched laser, extreme ultraviolet pulsed plasma, and a flash lamp, and
   the pulse timing of the light source is an integer multiple of the line shift of the time domain integration sensor.

6. The inspection system of claim 1, wherein:
   the light source is at least one of an excimer laser, a q-switched laser, extreme ultraviolet pulsed plasma, and a flash lamp, and
   the control system is in communication with the light source timing control.

7. The inspection system of claim 1, wherein:
   the pulse timing of the light source is an integer multiple of the line shift of the time domain integration sensor, and
   the control system is in communication with the light source timing control.

8. The inspection system of claim 1, wherein:
   the light source is at least one of an excimer laser, a q-switched laser, extreme ultraviolet pulsed plasma, and a flash lamp,
   the pulse timing of the light source is an integer multiple of the line shift of the time domain integration sensor, and
   the control system is in communication with the light source timing control.

9. The inspection system of claim 1, wherein the pulse timing of the light source is an non-integer multiple of the line shift of the time domain integration sensor.

10. The inspection system of claim 1, wherein:
    the light source is at least one of an excimer laser, a q-switched laser, extreme ultraviolet pulsed plasma, and a flash lamp, and
    the pulse timing of the light source is an non-integer multiple of the line shift of the time domain integration sensor.

11. The inspection system of claim 1, wherein:
    the control system is in communication with the light source timing control, and
    the pulse timing of the light source is an non-integer multiple of the line shift of the time domain integration sensor.

12. The inspection system of claim 1, wherein the pulse timing is from about 100 hertz to about 300 kilohertz.

13. An inspection system for creating images of a substrate, the inspection system comprising:
    a light source for directing an incident light onto the substrate wherein the pulse timing is an integer multiple of the line shift of the time domain integration sensor,
    a stage for holding the substrate and moving the substrate under the incident light, the substrate thereby reflecting the incident light as a reflected light,
    a stage position sensor for reporting a position of the stage,
    a stage position control for controlling the position of the stage,
    a time domain integration sensor for receiving the reflected light,
    a time domain integration sensor timing control for controlling a line shift of the time domain integration sensor, and
    a control system in communication with the stage position control and the time delay integration sensor timing control, for setting the position of the stage and the line shift of the time delay integration sensor, such that the stage and the time delay integration sensor integrates within a single line shift reflected light from more than one pulse of the incident light from the light source to form an image.

14. The inspection system of claim 13, wherein the light source is at least one of an excimer laser, a q-switched laser, extreme ultraviolet pulsed plasma, and a flash lamp.

15. The inspection system of claim 13, wherein the pulse timing is from about 100 hertz to about 300 kilohertz.

16. An inspection system for creating images of a substrate, the inspection system comprising:
    a light source for directing an incident light onto the substrate wherein the pulse timing is approximately an integer multiple of the line shift of the time domain integration sensor., a stage for holding the substrate and moving the substrate under the incident light, the substrate thereby reflecting the incident light as a reflected light, a stage position sensor for reporting a position of the stage, a stage position control for controlling the position of the stage, a time domain integration sensor for receiving the reflected light, a time domain integration sensor timing control for controlling a line shift of the time domain integration sensor, and a control system in communication with the light source, stage position control and the time delay integration sensor timing control, for setting the position of the stage and the line shift of the time delay integration sensor, such that the stage and the time delay integration sensor integrates within a single line shift reflected light from more than one pulse of the incident light from the light source to form an image and the number of light pulses in a frame can be counted.

17. The inspection system of claim 16, wherein the light source is at least one of an excimer laser, a q-switched laser, extreme ultraviolet pulsed plasma, and a flash lamp.

18. The inspection system of claim 16, wherein the pulse timing is from about 100 hertz to about 300 kilohertz.

* * * * *